United States Patent
McGraw

(10) Patent No.: US 9,200,492 B2
(45) Date of Patent: Dec. 1, 2015

(54) SOIL SAMPLER

(71) Applicant: Thomas V. McGraw, Buffalo Lake, MN (US)

(72) Inventor: Thomas V. McGraw, Buffalo Lake, MN (US)

(73) Assignee: DUO LIFT MANUFACTURING CO., INC., Columbus, NE (US)

( * ) Notice: Subject to any disclaimer, the term of this patent is extended or adjusted under 35 U.S.C. 154(b) by 254 days.

(21) Appl. No.: 13/852,790

(22) Filed: Mar. 28, 2013

(65) Prior Publication Data

US 2013/0319763 A1 Dec. 5, 2013

Related U.S. Application Data

(60) Provisional application No. 61/655,111, filed on Jun. 4, 2012.

(51) Int. Cl.
*G01N 1/00* (2006.01)
*E21B 25/00* (2006.01)
*G01N 33/24* (2006.01)

(52) U.S. Cl.
CPC .......... *E21B 25/00* (2013.01); *G01N 2033/245* (2013.01)

(58) Field of Classification Search
CPC .......................... G01N 2033/245; E21B 25/00
USPC ................ 175/20; 73/863, 864, 23.41, 61.55, 73/61.59, 61.68
See application file for complete search history.

(56) References Cited

U.S. PATENT DOCUMENTS

| | | | | |
|---|---|---|---|---|
| 3,264,877 A * | 8/1966 | Boxrud | ................... | E21B 49/02 172/22 |
| 4,714,196 A | 12/1987 | McEachern et al. | | |
| 5,247,761 A | 9/1993 | Miles et al. | | |
| 5,741,983 A * | 4/1998 | Skotnikov | ............ | A01B 79/005 175/20 |
| 6,360,829 B1 * | 3/2002 | Naber et al. | ..................... | 175/20 |
| 7,255,016 B2 * | 8/2007 | Burton | ....................... | 73/864.45 |
| 7,552,654 B2 | 6/2009 | Burton | | |
| 7,827,873 B2 * | 11/2010 | Burton | .................... | E21B 7/027 173/19 |
| 8,613,234 B1 * | 12/2013 | Harrell | ..................... | G01N 1/08 172/22 |
| 8,955,401 B1 | 2/2015 | Burton | | |

* cited by examiner

*Primary Examiner* — John Fitzgerald
*Assistant Examiner* — Truong Phan
(74) *Attorney, Agent, or Firm* — Dennis L. Thomte; Thomte Patent Law Office LLC

(57) ABSTRACT

A vehicle carrying apparatus for generating soil samples. Means are mounted to the vehicle for collecting multiple soil probes. Means are provided for conveying soil probes from relative positions at which they are disposed to a distributor generally at the centerline of the vehicle. A circular array of receiving stations are provided for sequentially receiving the soil probes.

1 Claim, 10 Drawing Sheets

SOIL SAMPLER

CROSS-REFERENCE TO RELATED APPLICATIONS

This is a regular application filed under 35 U.S.C. 111(a) claiming priority, under 35 U.S.C. §119(e)(1), of provisional application Ser. No. 61/655,111, previously filed Jun. 4, 2012, under 35 U.S.C. §111(b).

TECHNICAL FIELD

The present invention deals broadly with the field of agronomy. More narrowly, however, it deals with apparatus and methods for assessing the nutrient level and composition characteristics of the soil in a farm field. The apparatus and method in accordance with the present invention deal with taking soil sample cores in order to ascertain the appropriateness of a field for a particular use. Specific advantages include, among others: consistent depth and placement from row (quality), functioning in partially frozen, dried out and hard soils, and generation of consistent bulk density of cores in loose soil.

BACKGROUND OF THE INVENTION

It is the objective of agriculture to optimize the productive capacity of land designated for a particular purpose. The grower will, therefore, attempt to provide, in each plot of soil, the amount of fertilizer and other nutrients and additives that will render the plot ideal for the crop that is to be sown. The harvest taken from the land is, thereby, maximized. A grower, not having information as to the constituency of the soil, may not properly utilize agents applied to the field. If the grower is ignorant of what the current status of nutrients in the soil is, he cannot know how much fertilizer or other additives should be infused into the field.

The amount of existent nutrients and minerals will vary over time. A number of factors will bear upon how the soil is to be treated. These include prior applicants and history of prior-grown crops and previously applied additives. It is for these reasons that soil sampling is important.

Sampling of the soil can even be critical. The importance of testing soil samples is certainly readily apparent to the grower. It is, therefore, typical for the grower to take samples from various locations on an agricultural field. The samples consist of multiple soil extractions or "cores" obtained using probes at particular locations in the field. These samples are then analyzed to determine the level of the various nutrients and minerals. It is also important to know the level of compaction of the soil in various regions.

Solutions have been proposed to improve and make more efficient the process of taking soil samples. U.S. Pat. No. 7,827,873, issued to James D. Burton on Nov. 9, 2010 for an invention entitled SOIL SAMPLING APPARATUS AND METHOD, for example, illustrates an apparatus which automatically collects soil samples. The apparatus is run over a field where certain information is sought to be obtained. The apparatus includes a sampling assembly that rotates on a track. The probe of the assembly extends through the track and into the ground. The probe is retracted on each revolution of the track. The assembly is hinged and guided along the track in order to minimize soil compaction as the probe rotates around the rear wheel of the apparatus. Soil cores are pneumatically transferred to a bagging assembly which is located in the tractor or other vehicle which pulls the sampling apparatus.

The apparatus of the '873 patent, however, has distinct shortcomings. Particularly relevant is the distribution of probes taken at the various locations in the field.

It is to the shortcomings of the prior art, as discussed hereinbefore, that the present invention is directed. It is an improved soil sampling device which minimizes the problems known in the prior art. More specific advantages and structures and methods to gain those advantages will be discussed in more depth hereinafter.

SUMMARY OF THE INVENTION

The present invention is a system for use in taking soil samples. The samples comprise analysis of a plurality of cores taken with probes from a field. That is, an aggregation of the cores obtained with the probes define the sample taken.

The system employs a vehicle for carrying the various hardware comprising the inventive apparatus. The vehicle can be a pickup truck having the system mounted in the bed of the vehicle and extending backward beyond the bumper thereof. The system includes means for collecting cores using multiple soil probes. It is intended that a plurality of probe collections means would be employed, said multiple collecting means being disposed generally symmetrically on opposite lateral sides of a centerline of the vehicle. The probe collecting means, in a preferred embodiment, can comprise generally tubular structures within which cores are collected as downward pressure is applied by the collecting means to the ground surface.

The invention further includes means for conveying the cores from the probe collecting means to a distributor generally at said centerline of the vehicle. In a preferred embodiment, such conveying means can take the form of one or more augers to move the collected material along a conduit.

An array which defines a plurality of receiving stations is provided. The array, which can be generally circular, is disposed for rotation and sequential reception of the collected material.

The invention further includes means for sequentially depositing a soil probe in a corresponding receiving station. Such receiving stations can take the form of paper bags in which the probes are received and maintained.

In the preferred embodiment, a computer controller can be employed to selectively operate the function of the system. When a pickup is the motive vehicle, the controller can be mounted in the cab and bed of the vehicle.

DETAILED DESCRIPTION OF THE INVENTION

Figure 1:
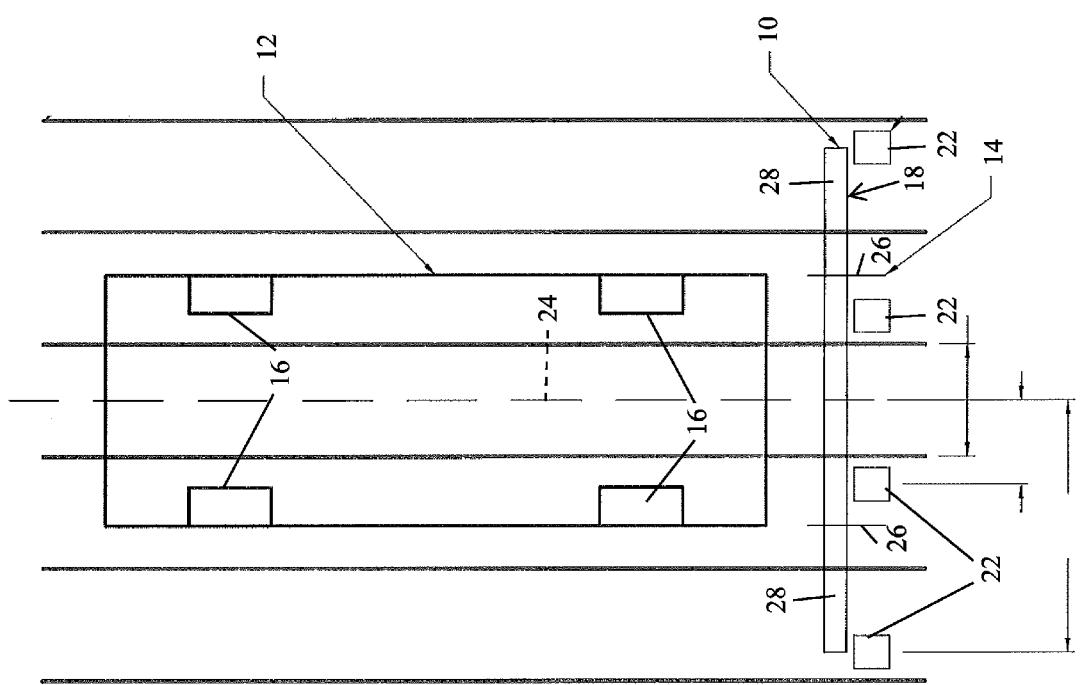
FIG. 1 is a top plan, schematic view illustrating the sampling unit and the frame by which the sampling unit is mounted to a vehicle.

Referring now to the drawing figures, wherein like reference numerals denote like elements throughout the several views, FIG. 1 illustrates the general construction of apparatus in accordance with the present invention. The apparatus is a system (10) for use in sampling soil for purposes of ascertaining the general consistency of the soil. FIG. 1 illustrates a vehicle (12) to which the operational structure can be mounted in order to make the system mobile. The vehicle is supported by a number of support elements. In the mobile embodiment, such structures would, it is envisioned, take the form of four wheels (16).

FIG. 1 also illustrates a sampling unit (14) mounted in the bed of the vehicle (12) and extending past the bumper. Mounting is accomplished by means of a frame (18) secured to the bed and the rear of the vehicle (12) in any appropriate manner.

The figures illustrate four sampling units for collecting soil cores (20). Operation of the soil probe collecting means would, it is envisioned, be in a manner known in the prior art. That is, a hollow, tubular collection unit (22) would be positioned at each station. The figures illustrate, as previously discussed, four such collecting means. The four collection units are shown as being aligned along an axis (not shown) generally transverse to the intended direction of motion imparted by the vehicle. The sampling units (14) are also shown as being substantially equidistant relative to one another. It will be understood, however, that such a construction is not exclusive. For example, while four sampling units (14) allow for greater coverage when soil probes (20) are being drawn, the use of two sampling units (14) straddling the centerline (24) of the vehicle (12) is contemplated within the scope of the invention. While narrower coverage of a farm field would be afforded when the vehicle/apparatus is in use, such a configuration would allow for easier storage of the vehicle (12).

It will be noted that the figures illustrate dual hinge points (26), one on either side of the vehicle centerline (24). This would allow for inward pivoting of frame lateral extensions (28) in order to narrow the overall structure when the apparatus is not in operation.

Figure 2:
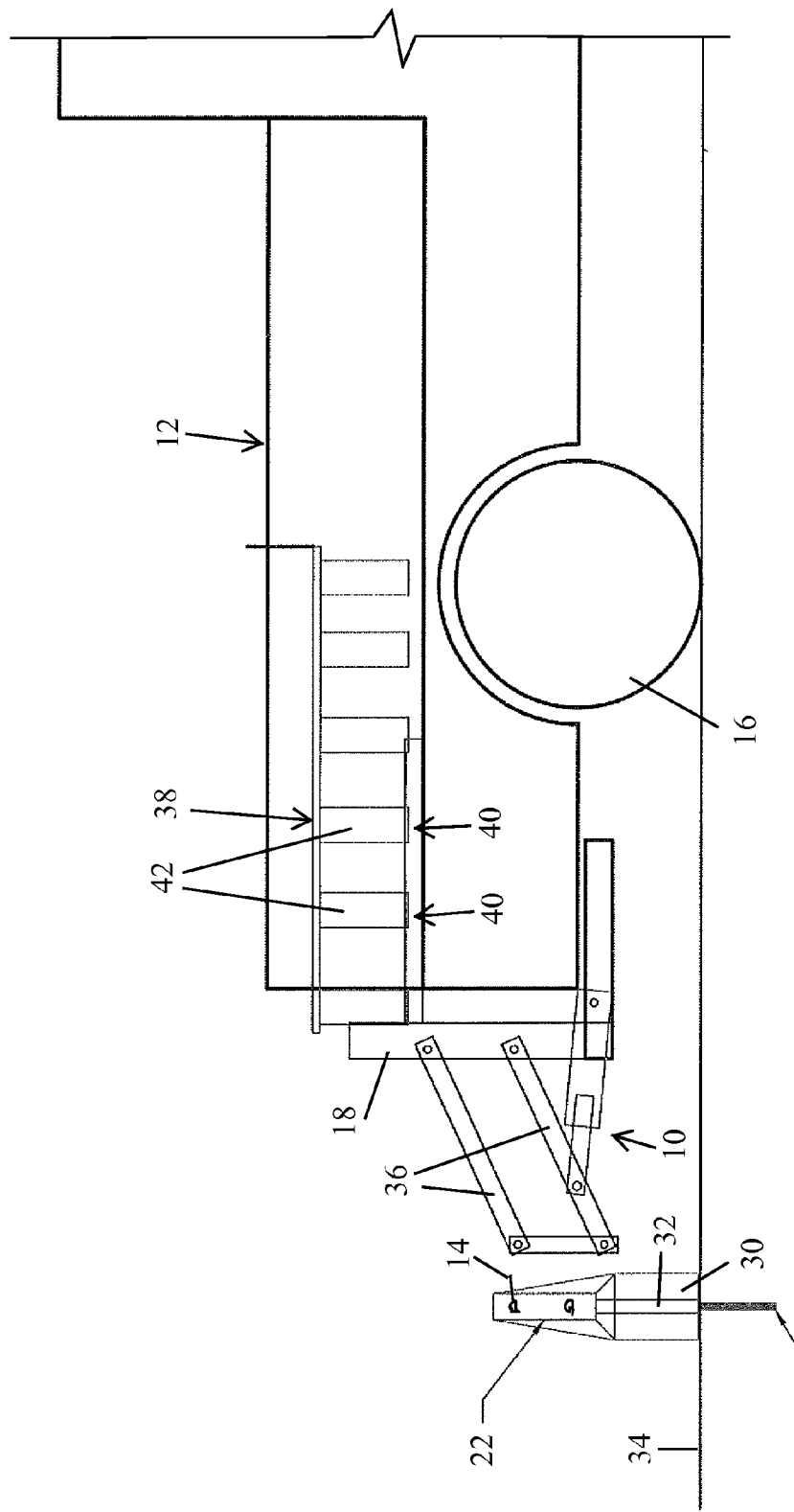
FIG. 2 is a side elevational, schematic view illustrating the sampling unit wherein the soil probe collecting means are extended.
Figure 3:
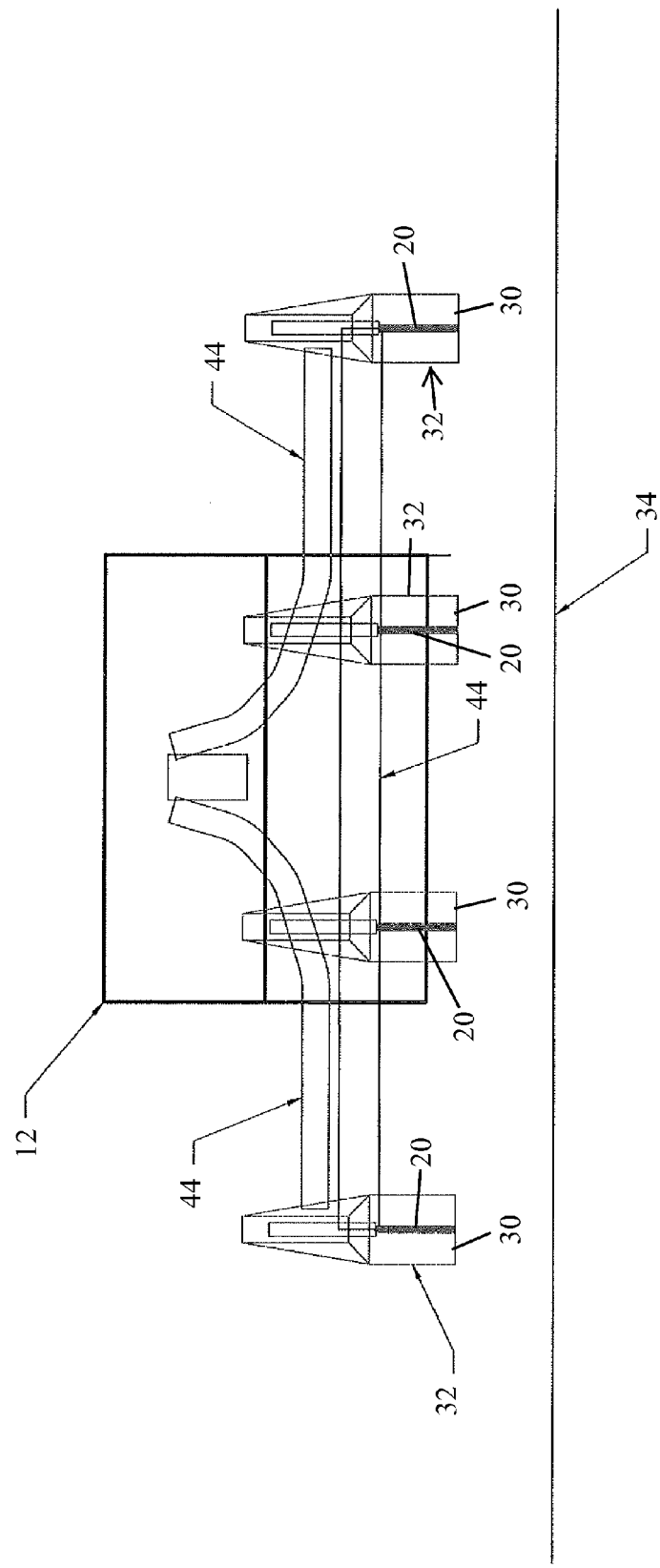
FIG. 3 is a rear elevational, schematic view illustrating the soil probe collecting means in retracted position.

FIG. 2 illustrates hydraulically operated shoes (30) which function to bring the probe cylinders (32) into engagement with the ground (34) and to actuate the cylinders (32) to effect immersion of the probe collecting structures in the ground (34) to draw corresponding cores with the probes (20). It is envisioned that the operation of linkages (36) between the frame (18) and the probe collection cylinder (32) would be hydraulically operated.

Figure 4:
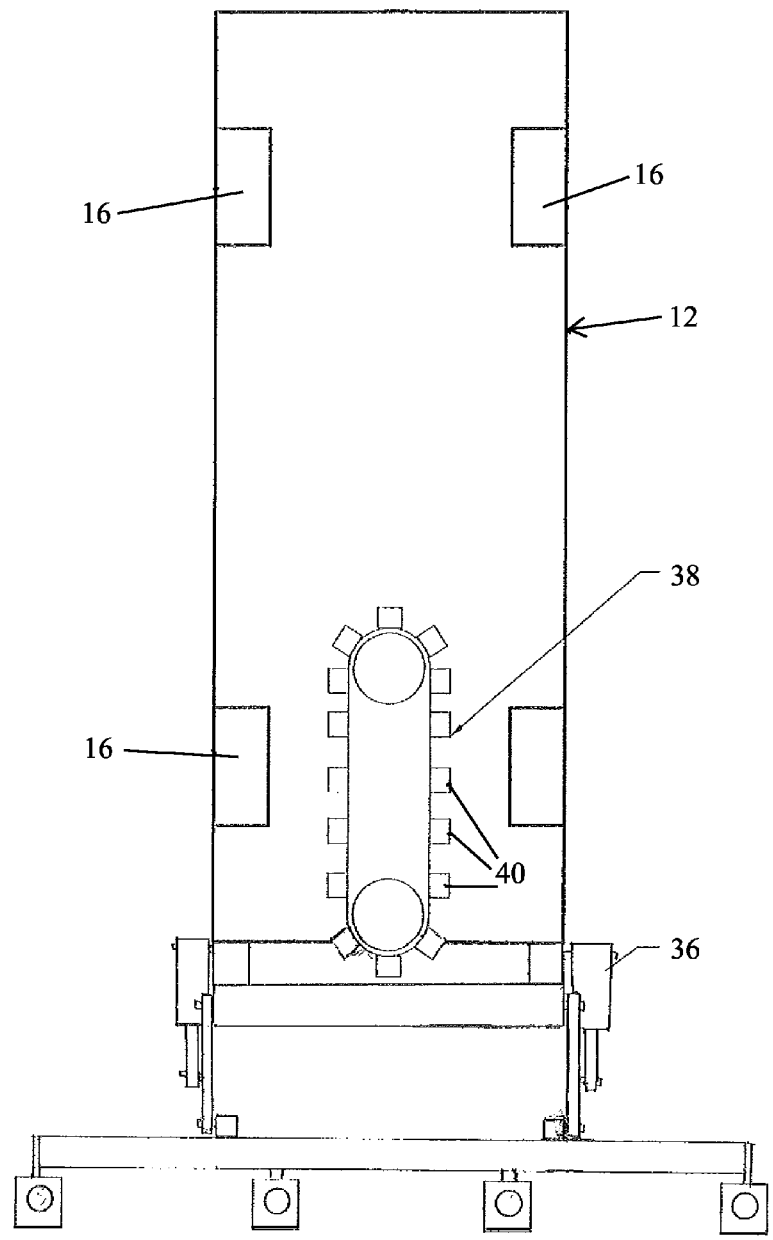
FIG. 4 is a top plan, schematic view illustrating lateral spacing of the various sample probe units.
Figure 5:
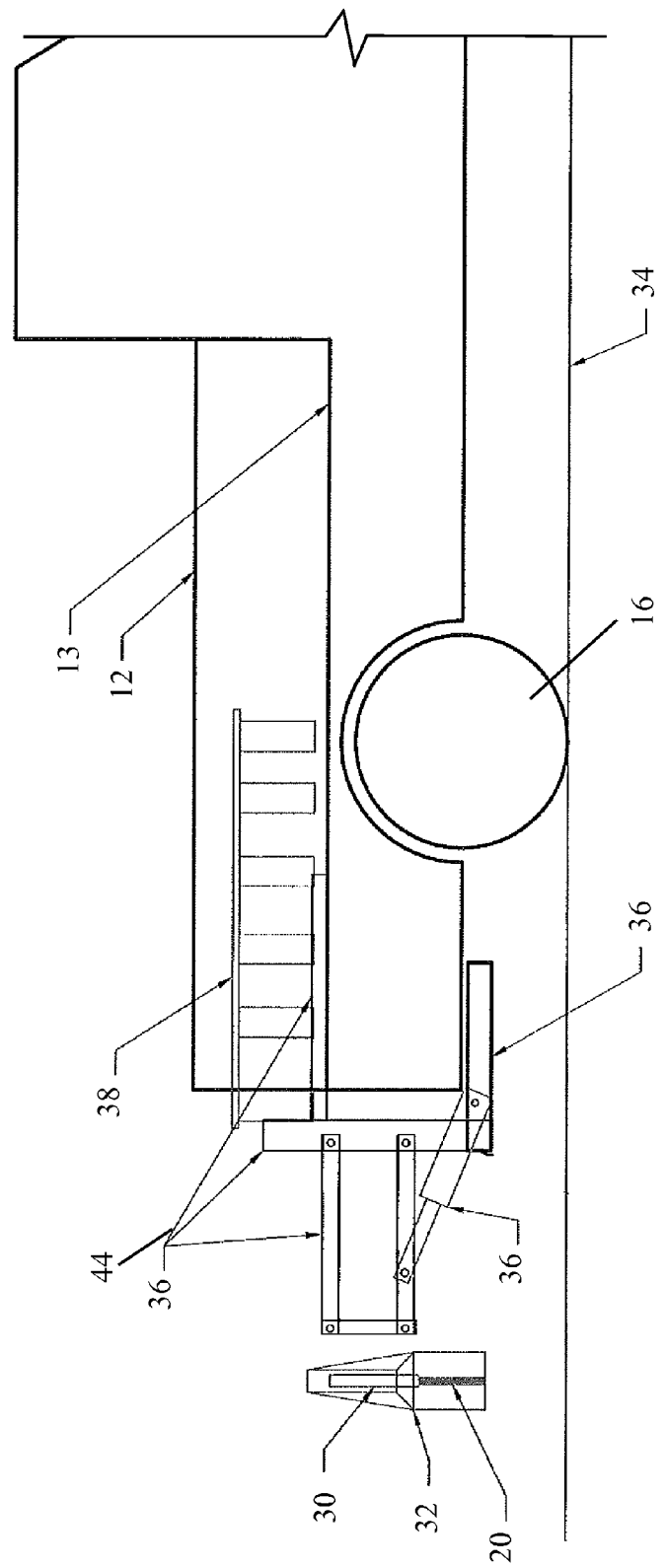
FIG. 5 is a side elevational, schematic view illustrating the soil probe collecting means in retracted positions.

The figures illustrate an array (38) which defines a plurality of receiving stations (40). These are provided to receive the soil cores (20) after they are drawn from the ground. The array (38) is shown best in FIG. 4 where it is shown positioned above the bed of the vehicle (12). It will be understood, however, that the path of the receiving stations (40) can be either elongated, as shown in the figures, or circular. In either case, the stations (40) are disposed for movement along the track and sequential receipt of the soil probes (20) in a receptacle (42) at each receiving station (40). Paper bags can be utilized as the recipient structure. This would serve to clean the system between fields, if desirable.

Figure 6:
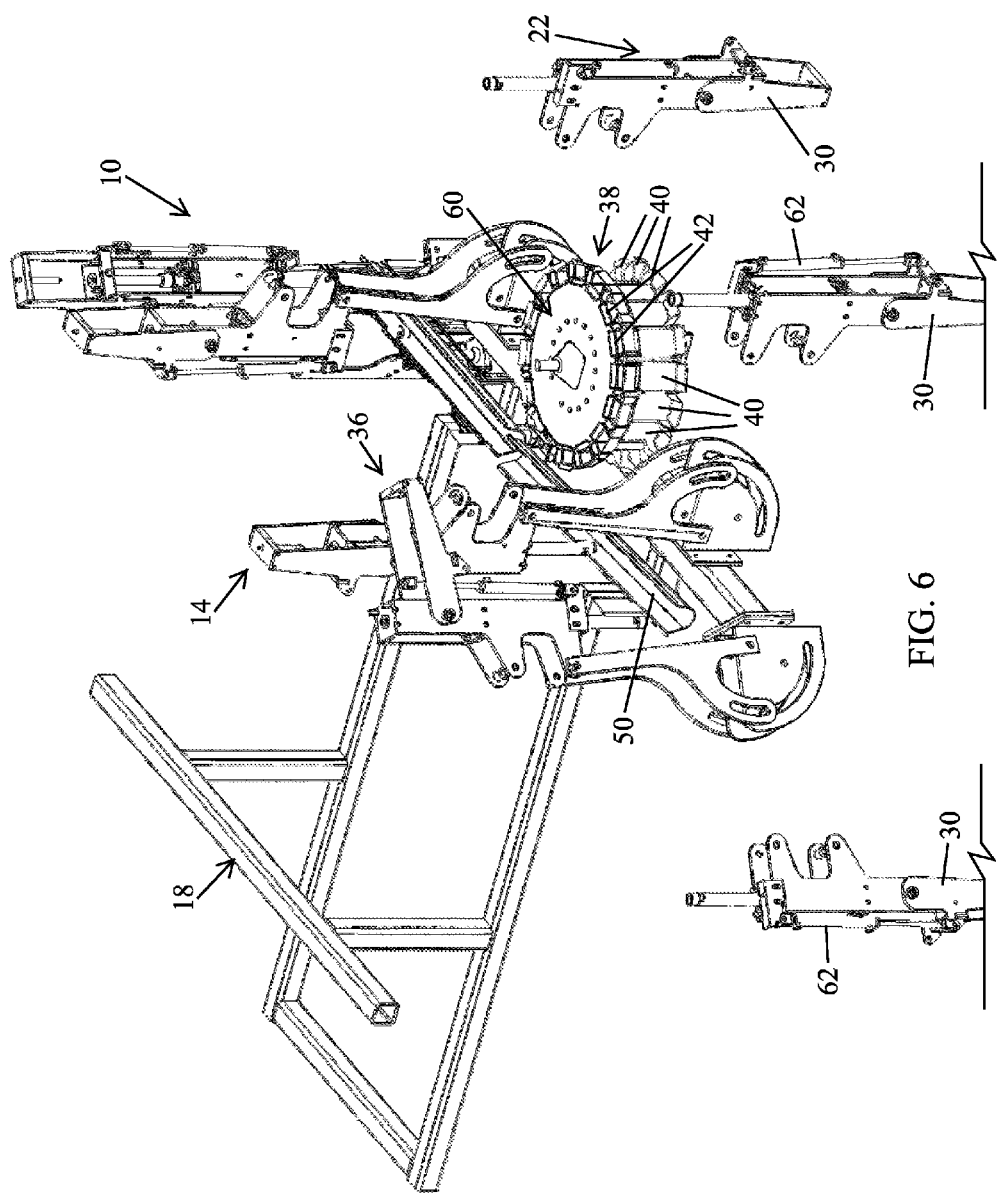
FIG. 6 is a structural perspective view of the system in accordance with the present invention.

With reference primarily now to FIGS. 6-10, a preferred system in accordance with the present invention will be described structurally. FIG. 6 illustrates a frame (18) which can be employed to mount the system to a motive vehicle (12) which processes along an intended track through the field. Typically, the frame (18) would be mounted in the bed of a pickup truck.

Figure 7:
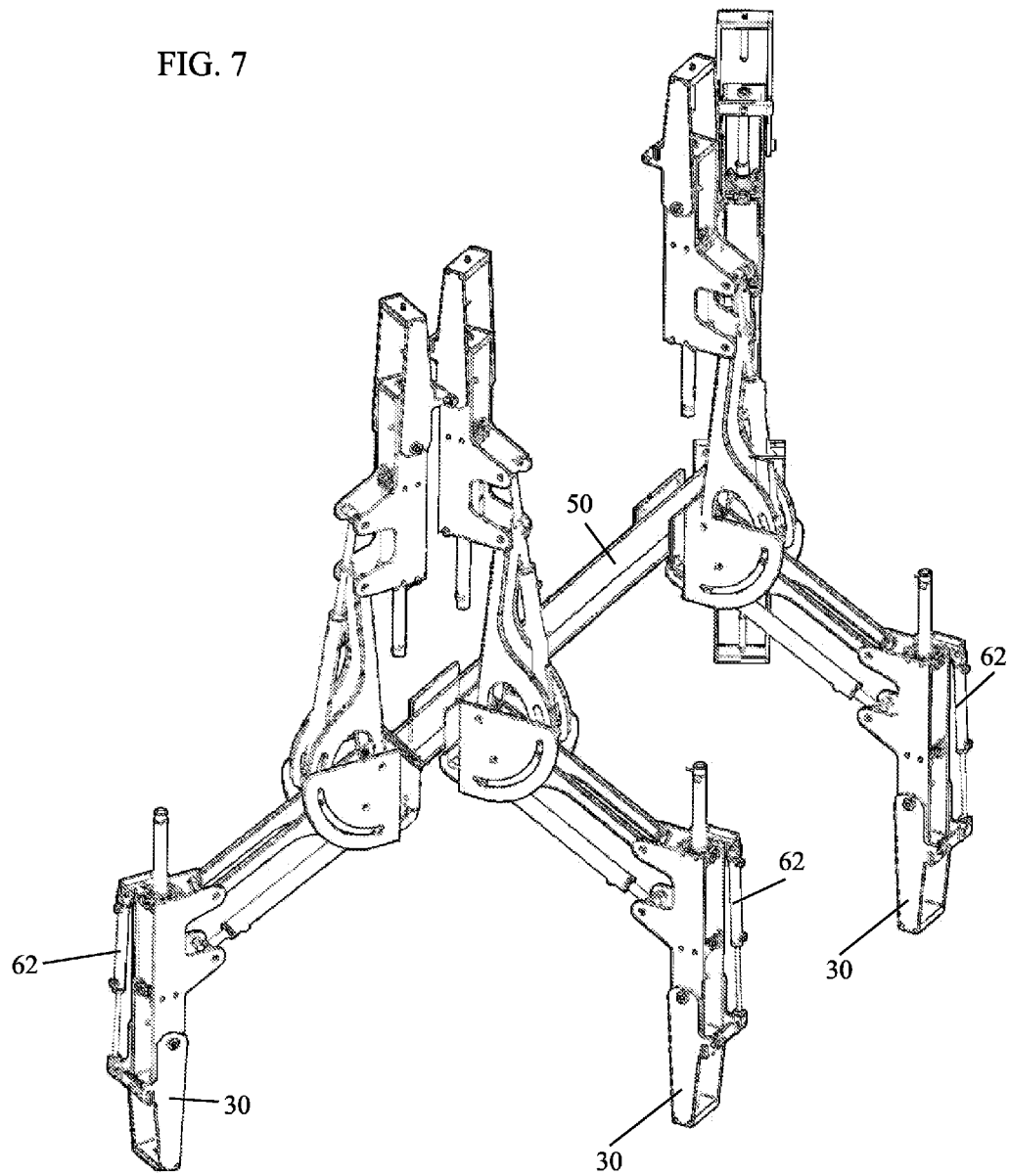
FIG. 7 is a view similar to FIG. 6 but wherein the system is facing in a somewhat forward direction.
Figure 8:
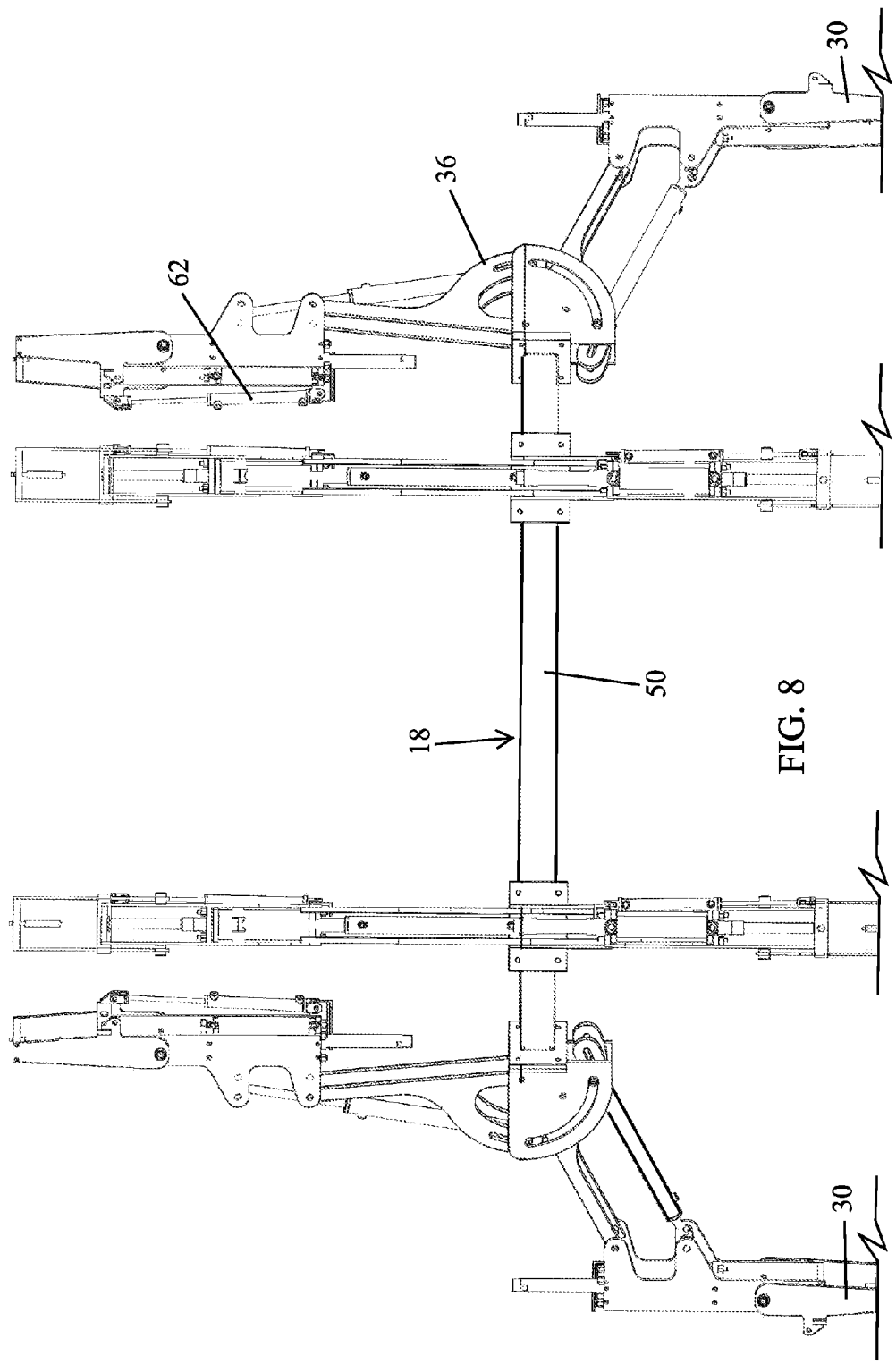
FIG. 8 is a rear elevational view of the system.
Figure 9:
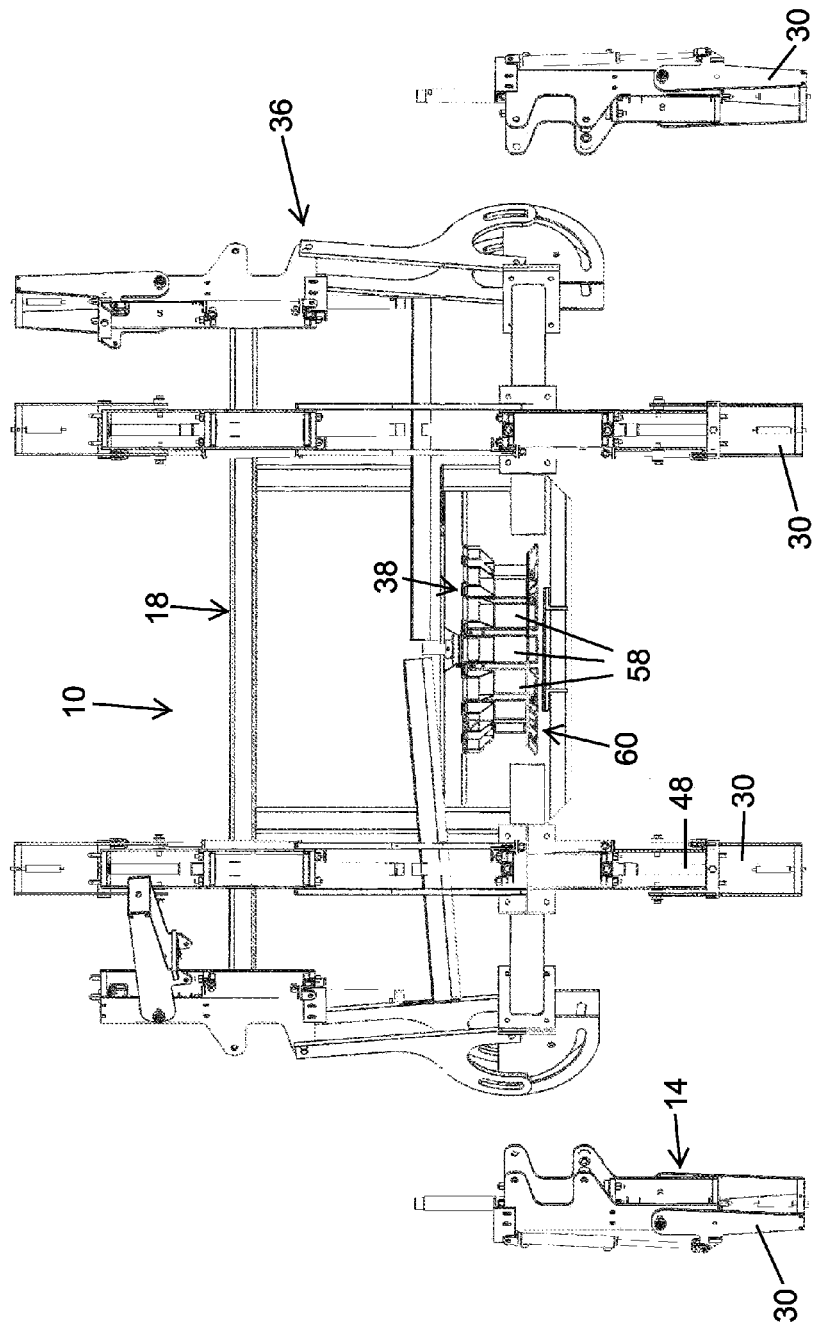
FIG. 9 is a rearward facing elevational view including the array of receiving stations.

FIGS. 6 and 7 illustrate multiple positions which can be occupied by shoes (46) mounting hollow tubular members (48) for burrowing into the soil to receive core material for subsequent assessment. FIG. 6 shows four of such shoe structures (46). The structures are shown in both rigged in and extended configurations. It will be understood that, when the system is not in use, the outriggers will be rotated to a rigged in position so as not to be configured such that movement of the vehicle (12) would be obstructed. During operation of the structures (36), wherein probe material is taken from the ground, the linkage structures, which are actuated hydraulically, are rigged out.

The figures illustrate a conduit (50) into which collected material dispensed out of the probe material collection means is received. The point of deposit (52) is spaced laterally from the centerline of the system. Means are provided therefore to convey the collected material from the point (52) at which it is deposited in the conduit to a chute (54) on the centerline. Auger means (44) can be utilized to effect such conveyance.

The conduit (50), at a point therealong, is provided with an aperture (56) through which the material, moved along the conduit (50) by the augers (44), is deposited in one of a plurality of receiving stations (58) identified as a station corresponding to a particular core taken. The discharge aperture (56) is provided for this purpose. Collected material conveyed along the conduit will be discharged through this aperture (56).

Figure 10:
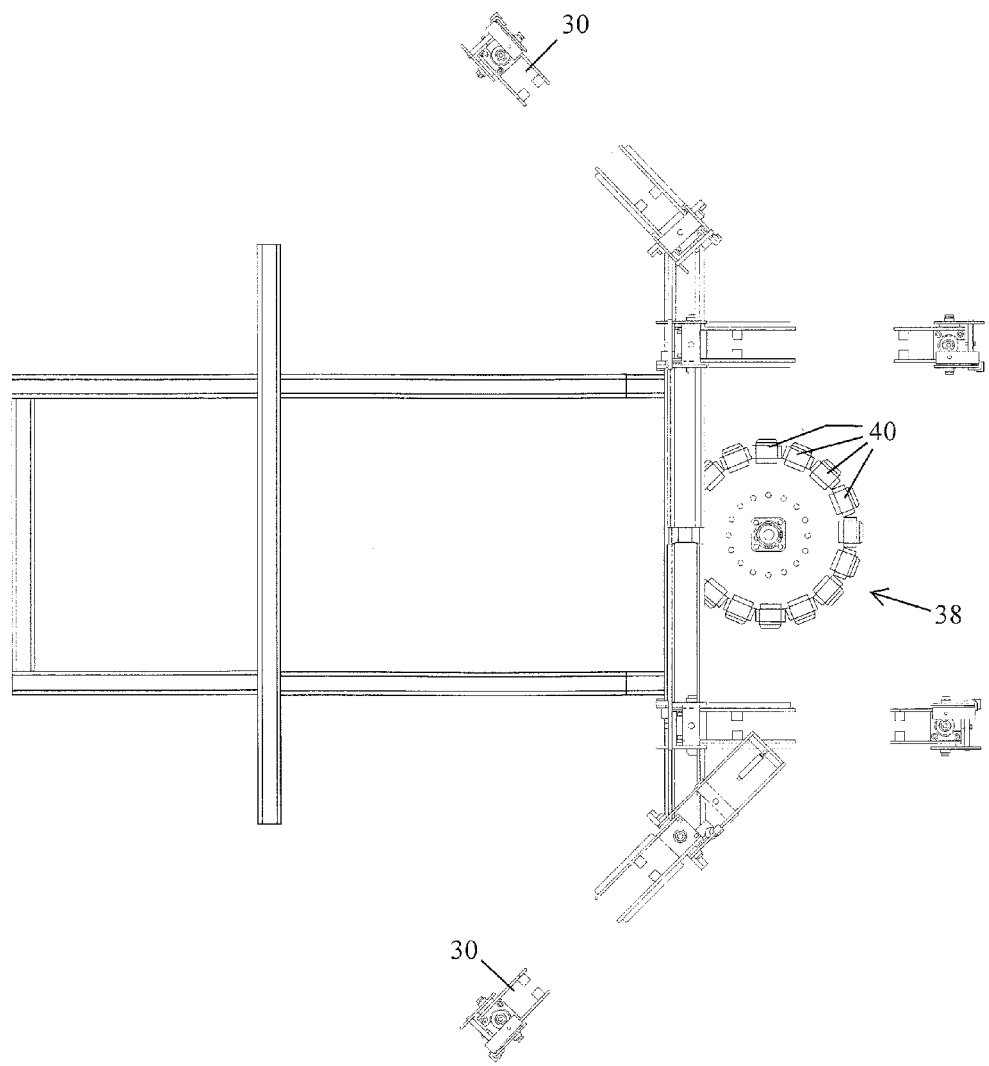
FIG. 10 is a top plan view showing the receiving station array.

The figures show an array of receiving stations (58) into which deposits are made. Each receiving station (58) identifies the location in the field from which the discharged core material is received. FIGS. 6 and 10 illustrate a generally circular carousel discharge station array (60). This configuration is not, however, exclusive. As seen in schematic FIGS. 1-5, the array can be elongated having a track running it through the bed within the pickup truck (12). It will be understood, however, that a generally circular carousel is a preferred embodiment.

It is important to coordinate the collected material taken from a certain location in the field with a particular discharge station.

The figures show a structure of the system wherein, when the system is not in use, hydraulic means can be provided to actuate pistons (62) that will effectuate drawing of the cores.

The system, as conceived and designed, functions by fitting the requirements of grid sampling using the center-point collection method. The probe clearing and cleaning system on an automatic soil sampler functions to work in glacial till soils and other soils that tend to stick to the probes. In order to control costs and make the system simpler, some soils such as silt, loam or sandy soil do not need clearing and cleaning system on the probe. If desired, therefore, the system could be manufactured without such a clearing and cleaning system.

It will be seen that there could be either a two-probe system or a four-probe system. In either case, a probe clearing and cleaning system can be employed as a function.

It will be understood that this disclosure is, in many respects, only illustrative. Changes may be made in details, particularly in matters of shape, size, material, and arrangement of parts without exceeding the scope of the invention. The scope of the invention is defined by the claims appended hereto.

What is claimed is:
1. An apparatus for generating soil samples, comprising:
   a mobile support platform having a first side, a second side, a forward end and a rearward end;
   a probe collector assembly mounted on said platform which includes a plurality of transversely spaced-apart soil probes which are configured to be inserted downwardly into the soil and to collect soil samples therein;
   a distributor mounted on said platform configured to receive the soil sampler from the soil probes; and
   a plurality of receiving stations on said platform which are configured for rotation and sequential receipt of the soil samples from said distributor.

* * * * *